United States Patent [19]

Pierce et al.

[11] Patent Number: 4,643,839

[45] Date of Patent: Feb. 17, 1987

[54] SILICONE REACTION PRODUCTS AND GLYCOL COMPOSITIONS CONTAINING THE PRODUCTS

[75] Inventors: Richard A. Pierce, Lake Jackson; David A. Wilson, Richwood, both of Tex.

[73] Assignee: The Dow Chemical Company, Midland, Mich.

[21] Appl. No.: 600,933

[22] Filed: Apr. 16, 1984

[51] Int. Cl.$^4$ ............................ C09K 5/00; C07F 7/10
[52] U.S. Cl. ...................................... 252/75; 252/78.3; 524/838; 525/474; 528/25; 528/38; 556/404; 556/405; 556/413; 556/424
[58] Field of Search ................ 252/75, 78.3; 556/404, 556/405, 413, 424; 524/838; 525/474; 528/25, 38

[56] References Cited

U.S. PATENT DOCUMENTS

| | | | |
|---|---|---|---|
| 3,121,692 | 2/1964 | Morehouse et al. | 252/75 |
| 3,282,846 | 11/1966 | Scott | 252/75 |
| 3,340,001 | 9/1967 | Thornhill | 252/75 |
| 3,362,910 | 1/1968 | Ordelt et al. | 252/75 |
| 3,716,569 | 2/1973 | Redmore et al. | 556/405 |
| 3,751,371 | 8/1973 | Redmore et al. | 252/175 |
| 3,816,184 | 6/1974 | Redmore et al. | 148/6.15 R |
| 4,367,154 | 1/1983 | Jernigan | 252/78.3 |

*Primary Examiner*—Robert A. Wax
*Attorney, Agent, or Firm*—Benjamin G. Colley

[57] ABSTRACT

The reaction product of phosphorous acid, formaldehyde, and monomeric or polymeric alkoxysilanes having one or more aminoalkylene groups are useful as gelation inhibitors for aqueous glycol solutions.

9 Claims, No Drawings

SILICONE REACTION PRODUCTS AND GLYCOL COMPOSITIONS CONTAINING THE PRODUCTS

BACKGROUND OF THE INVENTION

U.S. Pat. Nos. 3,716,569; 3,751,371; and 3,816,184 all assigned to Petrolite Corporation, disclose silicon-containing aminomethyl, or substituted aminomethyl phosphonic acids and derivatives as scale inhibitors and corrosion inhibitors. The compounds described in these inventions are prepared by first adding a mixture of water, phosphorous acid, and hydrochloric acid to an aminoalkyltrialkoxysilane, then heating this mixture and adding formaldehyde. The composition of this invention differs from that disclosed in the above Petrolite patents in the order of addition of the reagents and in the molar ratios of the reactants.

This invention relates to silicone reaction products that are obtained by reacting phosphorous acid, formaldehyde, and alkoxysilanes containing one or more aminoalkylene groups. These silicone products have been found to be useful to inhibit the gelation of aqueous silicate solutions and particularly aqueous glycol solutions containing alkali metal silicate.

The stabilization of aqueous silicate solutions with various siliconates has been reveiwed by E. P. Plueddenann in the book "Silane Coupling Agents" Plenum Publishing Co. 1982 pages 66-73.

In U.S. Pat. No. 4,367,154 there is disclosed the stabilization of aqueous glycol solutions with the reaction product of the reaction between 3-chloropropyl alkoxysilanes with dimethyl methyl phosphonate. The reaction products of this invention offer a significant cost advantage over these known stabilizers.

The Petrolite patents teach the use of equimolar amounts of formaldehyde and phosphorous acid for the preparation of their composition. In contrast, the composition of this invention is prepared by always using more formaldehyde than phosphorous acid, i.e., the molar ratio of formaldehyde to phosphorous acid is always greater than one. This excess of formaldehyde over phosphorous acid is believed to increase the possibility of methylene coupling between amines as illustrated below:

$O_{1.5}Si-CH_2-CH_2-CH_2-NH-CH_2-CH_2-NH_2 + H_2C(O) \rightarrow CH_2(NH-CH_2-CH_2-NH-CH_2-CH_2-CH_2-Si\,O_{1.5})_2 + H_2O$.

This allows an increase in the size of the alkyl portion of the silane which results in more efficient silicate stabilization, by shielding the silicate moieties with the divalent silane.

SUMMARY OF THE INVENTION

It has been found that the reaction products of phosphorous acid, formaldehyde and monomeric or polymeric alkoxysilanes having one or more aminoalkylene groups are useful in small and/or effective amounts to improve the gelation resistance of single phase glycol compositions containing alkali metal silicates.

The silicone reaction product of this invention is the product produced by heating an acidic solution comprising water, phosphorous acid, and formaldehyde until a temperature greater than about 50° C. and up to the reflux temperature is reached and a member of the group consisting of (1) monomeric alkoxysilanes having one or more aminoalkylene groups (2) oligomers, and polymers thereof, and (3) mixtures of (1) and (2) is then reacted with said heated solution.

The above product, which is believed to contain free phosphonic acid groups, is rendered even more effective by reacting or neutralizing the acidic reaction product with alkali metal hydroxides to form the alkali metal salts thereof.

A further aspect of the present invention is the aqueous glycol solution having the composition 85 to 98 percent by weight of an alkylene glycol, an alkylene glycol ether, or mixtures thereof, an amount effective to reduce metallic corrosion of an alkali metal silicate, and an amount of the above silicone reaction product effective to reduce gelation of said silicate.

These anti-gelation additives are effective in the presence of the other well-known corrosion inhibitors generally present in such compositions such as alkali metal borates, mercaptobenzotriazoles, nitrates, nitrites, phosphates, benzoates and the like.

DETAILED DESCRIPTION OF THE INVENTION

The glycols and glycol ethers which can be used in the present composition are (1) glycols such as ethylene glycol, diethylene glycol, propylene glycol, dipropylene glycol, (2) glycol monoethers such as the methyl, ethyl, propyl and butyl ether of ethylene glycol, diethylene glycol, propylene glycol and dipropylene glycol, and (3) glycol diethers such as the methyl and ethyl diethers of ethylene glycol, diethylene glycol, and dipropylene glycol.

Ethylene glycol, propylene glycol, and the monomethyl ether of propylene glycol, i.e., methoxypropanol are particularly preferred.

The following are examples of known corrosion inhibitors and additives which can be used in the present invention in conjunction with the above reaction products.

Alkali metal silicates such as sodium metasilicate, potassium metasilicate, lithium metasilicate, and the like.

Alkali metal borates such as sodium tetraborate, potassium tetraborate, sodium metaborate, and potassium metaborate.

Alkali metal mercaptobenzothiazoles, and alkali metal tolyltriazoles.

Alkali metal nitrates such as sodium nitrate, potassium nitrate, and alkali metal nitrites such as potassium and sodium nitrite.

Alkali metal phosphates such as sodium phosphate and potassium phosphate, alkali metal benzoates, and various dyes.

In the process of making the compositions of this invention, one or more of the above glycols are mixed with one of the above non-silicate corrosion inhibitors and sufficient amounts of mercaptobenzothiazoles, tolyltriazoles, nitrates, and phosphate inhibitors necessary for corrosion protection. The pH of the solution is then adjusted to the desired pH range of 5-12, and preferably 8-11, by adding a basic inorganic compound in aqueous solution such as an alkali metal hydroxide, carbonate, or phosphate. One of the above alkali metal silicates is then added to produce a corrosion and gelation resistant glycol composition. An effective amount of the reaction products can be added anytime during the above process.

The use of the above corrosion inhibitors when used in a corrosion inhibiting amount is well known in the prior art. Of course, this amount will vary for each inhibitor. In general the amounts used for the silicates and borates are 0.025 to 1.0 percent by weight based on the total solution weight of silicates and 0.1 to 2.0 percent by weight of borates. Preferably, these ranges are 0.05 to 0.50 percent for the silicates and 0.5 to 1.6 percent for the borates.

An accelerated aging test was used in the examples and controls that follow to estimate the gelation resistance of the compositions. It was performed by placing a sample of the glycol composition in an oven controlled at 80° C. and measuring the number of days before the composition first begins to gel.

The silicone reaction products of this invention are prepared by heating a solution of water, phosphorous acid and formaldehyde until a temperature greater than about 50° C. is reached. Preferably the temperature is in the range of 60° C. to the reflux temperature at atmospheric pressure. A pressurized reaction vessel may be used if desired to lower the temperature but no special advantage is obtained thereby.

The heated solution has a pH range from 0.1 to 3 and preferably 0.1 to 1.0 and is obtained by adding the proper amount of a strong mineral acid such as hydrochloric, phosphoric, sulfuric, and mixtures thereof.

The next step is to react the heated solution with monomeric, oligomer or polymeric alkoxy silanes having one or more aminoalkylene groups. The monomeric silanes have the formula:

$$(RO)_{3-m} R_m^2—Si—A—NR^3H$$

where
R is an alkyl group of 1-4 carbons, or an alkoxyalkylene group of 2-8 carbons
$R^2$ is an alkyl group of 1-4 carbons, phenyl, or an aralkyl group of 7-10 carbons,
$R^3$ is H or an alkyl group of 1-4 carbons
A is a divalent alkylene group with or without amine nitrogen groups
m is 0-2.

Examples of useful compounds are
N-2-aminoethyl-3-aminopropyltrimethoxysilane
$H_2NCH_2CH_2NH(CH_2)_3Si(OMe)_3$
N-methyl-N-(2-aminoethyl)-3-aminopropyltrimethoxysilane

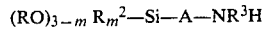
N-(2-aminoethyl)3-aminopropylmethyldimethoxysilane
$H_2NCH_2CH_2NH(CH_2)_3SiMe(OMe)_2$
N-2-aminoethyl-3-aminopropyltris-(2-ethylhexoxy)silane
$H_2N(CH_2)_2NH(CH_2)_3Si[OCH_2CH(C_4H_9)(C_2H_5)]_3$
3-aminopropyldimethylethoxysilane
$H_2N(CH_2)_3SiMe_2OEt$
3-aminopropylmethyldiethoxysilane
$H_2N(CH_2)_3SiMe(OEt)_2$
3-aminopropyltriethoxysilane
$H_2N(CH_2)_3Si(OEt)_3$
3-aminopropyltrimethoxysilane
$H_2N(CH_2)_3Si(OMe)_3$
4-aminobutyldimethylmethoxysilane
$H_2N(CH_2)_4SiMe_2OMe$
(aminoethylaminomethyl)phenethyltrimethoxysilane

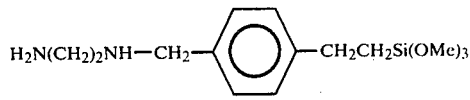

bis[3-(triethoxysilyl)propyl]amine
$[(EtO)_3Si—(CH_2)_3—]_2NH$
bis[3-(trimethoxysilyl)propyl]ethylenediamine
$[(MeO)_3Si—(CH_2)_3—NH—CH_2—]_2$
N-methylaminopropyltrimethoxysilane
$MeHN—(CH_2)_3—Si(OMe)_3$
trimethoxysilylpropyldiethylenetriamine
$H_2N(CH_2)_2NH(CH_2)_2NH(CH_2)_3Si(OMe)_3$.

It is to be noted that these compounds can also be used in the form of their oligomers and/or polymers.

This invention is further illustrated by the following non-limiting examples and controls.

EXAMPLES 1-9

To a 250 ml three neck flask fitted with a reflux condensor and dropping funnel was added deionized water, 70% phosphorous acid ($H_3PO_3$), 37% formaldehyde ($CH_2O$), and acid (HCl and/or $H_2SO_4$). This was stirred vigorously and heated to reflux. Then, 5.6 g (.025 mole) of N-2-aminoethyl-3-aminopropyltrimethoxysilane was added dropwise. The mixture was heated and stirred overnight. After the reaction cooled, a sample was either bottled as is or neutralized with 50% sodium hydroxide. These examples, including the amounts of the individual reagents, are listed in Table I.

Controls 1 and 2

These controls are offered for comparison purposes only. They were prepared according to U.S. Pat. No. 3,716,569. To a 500 ml three neck flask fitted with a reflux condensor and dropping funnel was added 55.6 g (.25 mole) of N-2-aminoethyl-3-aminopropyltrimethoxysilane. To this was added slowly a mixture of 70% phosphorous acid, deionized water, and concentrated hydrochloric acid. The mixture was heated to gentle reflux and 37% formaldehyde was added dropwise during one hour. The mixture was then heated for an additional hour to complete the reaction. These controls are also illustrated in Table I.

TABLE I

| Run | Code | $H_2O$ (g) | $H_3PO_3$ (mole) | $CH_2O$ (mole) | HCl (g) | $H_2SO_4$ (g) | 50% NaOH |
|---|---|---|---|---|---|---|---|
| Ex. 1 | 30210-7A | 50 | .038 | .075 | 5 | — | No |
| Ex. 2 | 30210-7B | 50 | .038 | .075 | 5 | — | Yes |
| Ex. 3 | 30210-14A | 50 | .025 | .075 | 5 | — | No |
| Ex. 4 | 30210-14B | 50 | .025 | .075 | 5 | — | Yes |
| Ex. 5 | 30210-37A | 50 | .038 | .075 | — | 5 | No |
| Ex. 6 | 30210-37B | 50 | .038 | .075 | — | 5 | Yes |
| Ex. 7 | 30753-34 | 13 | .038 | .075 | 2.5 | 2.5 | Yes |
| Ex. 8 | 31908-14 | 13 | .038 | .050 | 2.5 | 2.5 | Yes |
| Ex. 9 | 31908-15 | 13 | .038 | .100 | 2.5 | 2.5 | Yes |
| Control 1 | 31232-23A | 50 | .50 | .50 | 60 | — | No |
| Control 2 | 31908-16 | 50 | .25 | .25 | 60 | — | No |

Table II illustrates the comparative molar ratios for each of the examples described in Table I.

TABLE II

| Example | No. of amine H's in Silane (n) | equiv. of CH₂O | equiv. of H₃PO₃ |
|---|---|---|---|
| 1 | 3 | 3 | 1.5 |
| 2 | 3 | 3 | 1.5 |
| 3 | 3 | 3 | 1 |
| 4 | 3 | 3 | 1 |
| 5 | 3 | 3 | 1.5 |
| 6 | 3 | 3 | 1.5 |
| 7 | 3 | 3 | 1.5 |
| 8 | 3 | 2 | 1.5 |
| 9 | 3 | 4 | 1.5 |
| Control 1 | 3 | 2 | 2 |
| Control 2 | 3 | 1 | 1 |

EXAMPLES 10–18

A coolant formulation was prepared utilizing well-known corrosion inhibitors generally present in such compositions as alkali metal silicates, borates, mercaptobenzothiazoles, nitrates, nitrites, phosphates, benzoates, and the like. These compositions are well known in the prior art as is illustrated by U.S. Pat. Nos. 3,282,846, dated Nov. 1, 1966; 3,362,910, dated Jan. 9, 1968; and 3,340,001, dated Sept. 5, 1967. The coolant thus prepared was divided into 60 g aliquots and an amount of stabilizer added so that the concentration of elemental silicon in the coolant was 8 ppm irrespective of inorganic silicate. The gel stability of the original solution (control) as well as the stabilities of the coolants with the various stabilizers added are presented in Table III. The time in days is the amount of time before the first visible formation of a gel was observed.

TABLE III

| Example | Stabilizer | Stability at 80° C. (days) |
|---|---|---|
| Control 3 | None | 2 |
| 10 | prod. from Ex. 1 | 7 |
| 11 | prod. from Ex. 2 SS | 8 |
| 12 | prod. from Ex. 3 | 7 |
| 13 | prod. from Ex. 4 SS | 8 |
| 14 | prod. from Ex. 5 | 6 |
| 15 | prod. from Ex. 6 SS | 8 |
| 16 | prod. from Ex. 7 SS | 10 |
| 17 | prod. from Ex. 8 SS | 7 |
| 18 | prod. from Ex. 9 SS | 8 |
| Control 4 | prod. from Ex. Control 1 | 6 |
| Control 5 | prod. from Ex. Control 2 | 6 |

Notes: SS indicates the sodium salt of the reaction product.

It is to be noted that one day stability at 80° C. is approximately equal to 3.5 months at 25° C.

It is to be further noted that the sodium salt of the rection products are better than the free acid forms and are the preferred form.

We claim:

1. The silicone reaction product produced by
   (A) heating an acidic solution comprising water, phosphorous acid, and formaldehyde until a temperature greater than about 50° C. is reached wherein the molar ratio of formaldehyde to phosphorous acid is greater than one and,
   (B) reacting a member of the group consisting of (1) monomeric alkoxysilanes having one or more aminoalkylene groups (2) oligomers and polymers thereof, and (3) mixtures of (1) and (2) with said heated solution.

2. The reaction product of claim 1 which has been further reacted with sufficient alkali metal hydroxide to form the salts thereof.

3. The reaction product of claim 1 wherein the monomeric alkoxysilanes have the formula $$(RO)_{3-m} R^2_m—Si—A—NR^3H$$

where
R is an alkyl group of 1–4 carbons, or an alkoxyalkylene group of 2–8 carbons
$R^2$ is an alkyl group of 1–4 carbons, phenyl, or an aralkyl group of 7–10 carbons,
$R^3$ is H or an alkyl group of 1–4 carbons
A is a divalent alkylene group with or without amine nitrogen groups
m is 0–2.

4. A gelation resistant aqueous glycol composition comprising
   (A) 85 to 98 percent by weight of an alkylene glycol, an alkylene glycol ether, or mixtures thereof,
   (B) an amount effective to reduce metallic corrosion of an alkali metal silicate, and
   (C) an amount of the silicone product of claim 1, 2, or 3 effective to reduce gelation of said silicate.

5. The composition of claim 4 wherein the amount of alkali metal silicate used is 0.025 to 1.0 percent by weight and the amount of said silicone product used is that amount which will give greater than 1.6 parts per million of elemental silicon in said composition irrespective of said silicate.

6. The composition of claim 5 wherein the amount of said silicone product is that amount which will give from about 5 to about 10 parts per million of elemental silicon in said composition irrespective of said silicate.

7. A method for the preparation of a gelation resistant aqueous glycol composition containing one or more metallic corrosion inhibitors which comprises adding an effective amount of the reaction product of claim 1.

8. The method as set forth in claim 7 wherein the added reaction product is the reaction product of claim 2.

9. The method as set forth in claim 7 wherein the added reaction product is the reaction product of claim 3.

* * * * *